United States Patent [19]

Pantridge et al.

[11] 4,023,573
[45] May 17, 1977

[54] DEFIBRILLATOR

[76] Inventors: James Francis Pantridge, Colin House, Dunmurry, Co. Antrim; John Anderson, 38 Ardmore Road, Holywood, Co. Down, both of Ireland

[22] Filed: Oct. 28, 1975

[21] Appl. No.: 626,177

[30] Foreign Application Priority Data

Oct. 28, 1974 United Kingdom ............ 46464/74

[52] U.S. Cl. .......................... 128/419 D; 128/405
[51] Int. Cl.² .......................................... A61N 1/36
[58] Field of Search ............. 128/419 D, 404, 417, 128/405

[56] References Cited

UNITED STATES PATENTS

| | | | |
|---|---|---|---|
| 1,936,405 | 11/1933 | Mueller | 128/421 |
| 3,258,013 | 6/1966 | Druz | 128/419 D |

Primary Examiner—William E. Kamm
Attorney, Agent, or Firm—Karl W. Flocks

[57] ABSTRACT

A portable defibrillator to inflict an electric shock on patients comprises a pair of electrodes to be connected to the patient and a circuit to pass a shock of given magnitude and duration through the electrodes and patient, the circuit being contained in housings on which the electrodes are mounted so that the defibrillator is fully portable.

6 Claims, 4 Drawing Figures

DEFIBRILLATOR

BACKGROUND OF INVENTION

This invention relates to a defibrillator, and is particularly concerned with a portable defibrillator which is eaily transported and may be used in the field independently of mains electrical supply.

In the medical field defibrillators are used for the correction of cardiac arrest due to ventricular fibrillation. The principle requirement of a defibrillator is that it must be capable of delivering a controlled electric shock to the patient, this being acheived by applying electrodes connected to the device to the patient's body, generally across the patient's chest.

PRIOR ART

There is known a defibrillator of this type comprising a capacitor, charging means including a D.C. current source arranged to charge the capacitor to a given potential, an inductance and a pair of electrodes arranged to be connected to the capacitor, one by way of the inductance, whereby the capacitor may be discharged through a patient by means of the electrodes to deliver an electric shock to the patient, the capacitor and inductance being selected so that the discharge pulse has a given duration, peak value and rise time when the electrodes are connected across a load resistance which corresponds to that of a typical patient.

The source of electric power for the defibrillator may be a battery, so that the defibrillator may be independent of the mains supply and therefore portable. However this defibrillator has a certain bulk and weight because of the size of the electronic components which have hitherto been used and because these electronics are housed in a casing to which both electrodes are connected by leads. Such a device may be transported readily in an ambulance or the like but is not conveniently carried by hand for emergency use in the field.

GENERAL DESCRIPTION OF INVENTION

The present invention relates to a defibrillator of the type mentioned above but in which both electrodes are mounted on respective housings which may be placed in contact with the patient, the charging means, inductance, capacitor and any other electric components used in the defibrillator being contained in or on said housings so that the apparatus is fully portable.

In one preferred arrangement, the inductance which may comprise a conventional choke is mounted in one of the housings whereas substantially all of the other components are mounted in the other housing. The housing containing the choke may therefore be relatively small and, when not in use, may be attached by a clip or other means to the other housing so that the defibrillator is easily carried as a single unit, preferably by means of a handle attached to the main housing designed to allow carrying with one hand.

Known defibrillators have used the so-called "Lown" wave form for the electric output current from the electrodes during the infliction of a shock on the patient, this wave-form being named after the American physician, Bernard Lown, who did much early work on the development of such defibrillators. In such known devices the Lown wave-form peaks at some seven kilovolts and has a duration of some 4½ milliseconds. A further characteristic of wave-forms used previously has been the very short initial rise time of the wave-form being typically of the order of 500 microseconds. It has been found that such an output wave-form causes high peak currents through the patient during the shock and has resulted in damage to the myocardium. Further, since a given stored energy was transferred at a high voltage by the device high electrical losses in the system resulted in considerable inefficiency.

These problems can be avoided or alleviated by designing the defibrillator so that the voltage wave-form across the electrodes of the discharge pulse has a duration of between 10 and 16 miliseconds, a peak value of not more than 4 kV and a minimum rise time to that peak of 1000 microseconds when the electrodes are connected across a load resistance of from 50 to 75 ohms. Preferably the minimum rise time is about 1100 microseconds.

In a preferred embodiment the capacitor has a value of 50 microfarads and the inductance has a value of 50 millihenries and a resistance of 18 ohms.

DESCRIPTION OF PREFERRED EMBODIMENT

A defibrillator according to a preferred embodiment of the invention will now be described by way of example with reference to the accompanying drawings, in which.

Figure 1:
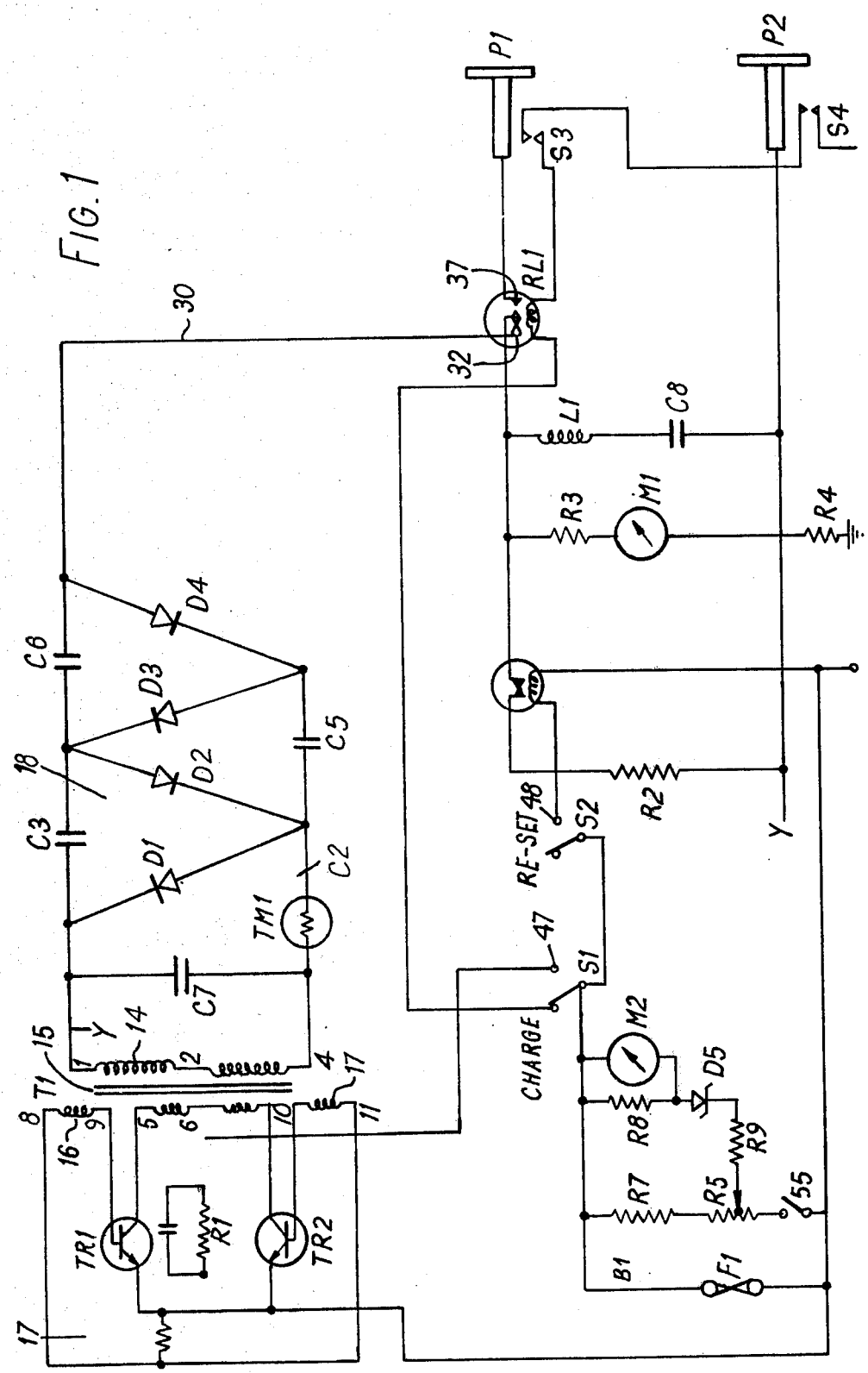
FIG. 1 is a circuit diagram of a defibrillator.

Referring first to FIG. 1, electric power is provided by a rechargeable nickel-cadmium cell of known type B1 giving about 20 volts potential. A push-pull oscillator circuit indicated generally at 11 including two transistors TR1 and TR2 takes power from the battery to produce an AC output which is taken from the oscillator by means of a secondary winding 14 of a toroidal transformer 15 in the output of the oscillator circuit.

Additional windings 16 and 17 of the transformer 15 provide the feed-back elements in the oscillator circuit which operates in a push-pull saturable core mode. The timing of the oscillator is dependent on the rate of core saturation in the transformer and the number of turns in the primary winding. The value of the base bias resistor which is common to the two transistors is chosen to ensure the optimum base current needed to achieve a sufficient final drive current in the secondary winding 14 of the transformer, for example 235 ohms. The oscillator operates at 20 KHz and the transformer ratio is such as to give an output voltage of 1 KV at peak.

The secondary winding 14 is connected to a voltage multiplier circuit indicated generally at 18 to give an output of four KV on the positive line 30 with respect to the earth line.

The output from the voltage multiplier is taken to a fixed contact 32 of a relay RL1. The movable contact of the relay RL1 is connected to one side of a shock energy storage capacitor C8, through a choke L1, the other side of capacitor $C_8$ connected to the earth line of the voltage multiplier. The movable contact of the relay RL1 is normally in contact with the contact 32 when the solenoid of the relay is deenergized. The other fixed contact 37 of the relay RL1 is connected to one $P_1$ of a pair of electrodes $P_1$ and $P_2$ by which the electric shock may be inflicted on the patient.

Normally open push-button switches $S_3$ and $S_4$ are provided with the electrodes $R_1$ and $P_2$ and arranged so that a user of the apparatus may close the switches when the electrodes are correctly placed across the patient. Switches $S_3$ and $S_4$ are in series with the solenoid of relay RL1 and with the battery B1 so that closing them energises the relay.

The positive terminal of the battery is connected to the blades of switches $S_1$ and $S_2$. In the position of $S_1$ shown in the drawing the solenoid of relay RL1 can be energised from the battery by switches $S_3$ and $S_4$. When switch $S_1$ is moved to its other position (with the blade in contact with stud 47), i.e. to "charge" position the oscillator is energised but the relay 36 cannot be operated. Thus when switch $S_1$ is set at "charge" the oscillator is brought into operation so that the capacitor $C_8$ is charged up to a potential of 5 KV, which typically takes about 7 seconds. When switch $S_1$ is returned to its non-charge position the charge held by the capacitor may be discharged through the patient by operation of switches $S_3$ and $S_4$.

Switch $S_2$ is arranged as a "re-set" switch which is inoperative in the position shown in the drawing. However, when the switch blade is moved into contact with stud 48 so that relay RL2 is energized, the capacitor $C_8$ is then discharged through a protective resistor $R_2$. This operation may be desirable for safety or other reasons.

A meter $M_1$ is provided in series with resistor $R_3$ and $R_4$ to indicate the charge level on the capacitor $C_8$. The meter is calibrated in terms of the stored electrical energy, in watt-seconds, thus enabling the operation to exercise control over the energy level of the shock inflicted. A second meter $M_2$ is arranged, by means of conventional circuitry, to indicate the energy state of the battery cells on operation of switch $S_5$.

The various electronic units and circuit components indicated in FIG. 1 are of types which are in themselves all well known in the electronics art and will not be described herein in further detail.

Figure 2:
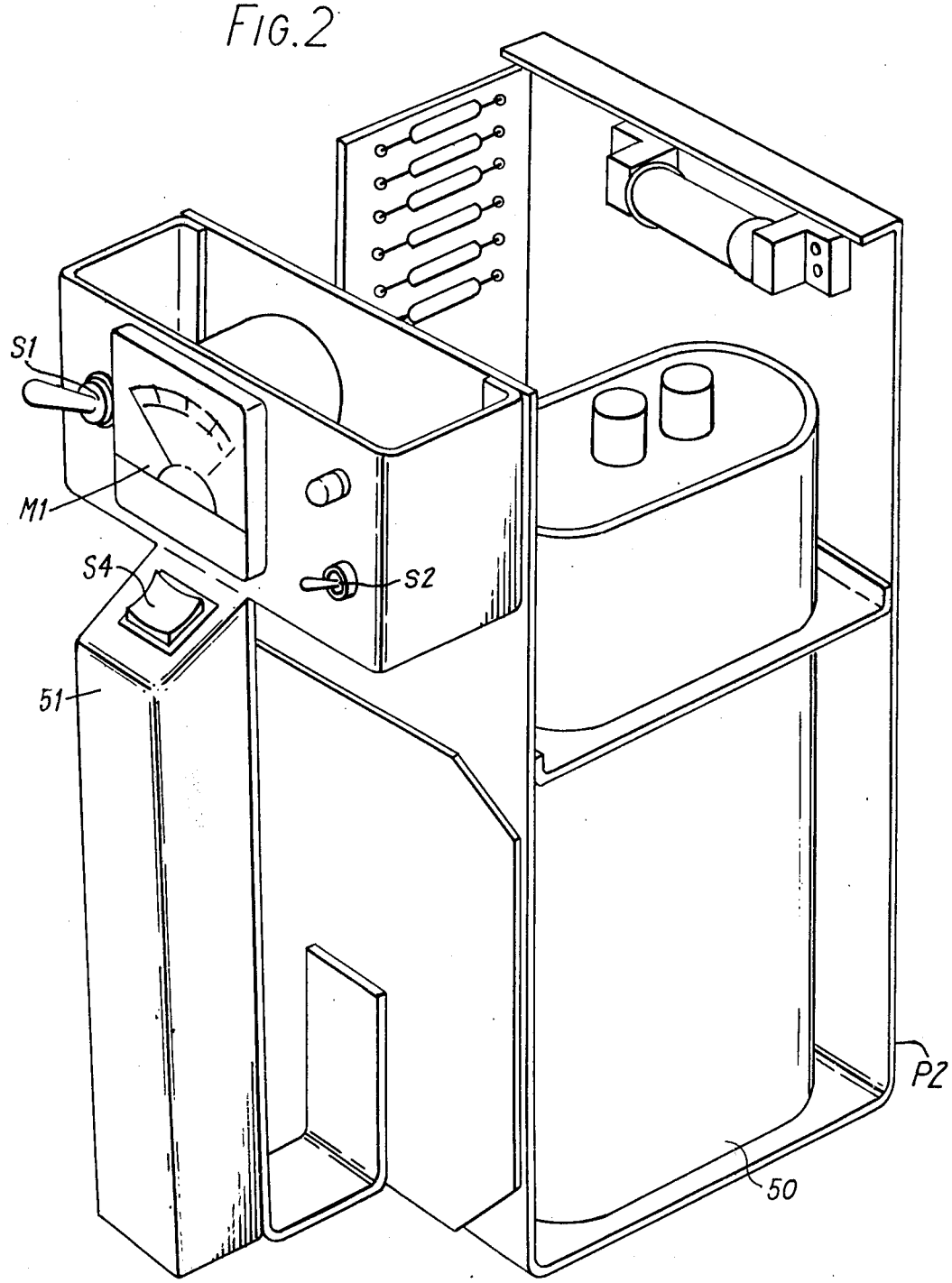
FIG. 2 is a partially cut-away housing of the defibrillator of FIG. 1.

One of the housings is shown in FIG. 2; this housing contains all the above-described electrical components apart from the electrode $P_1$, switch $S_3$, choke L1 and relay RL1. This housing has the approximate overall dimensions 20.6 × 10.0 × 15.2 cms and is provided with a handle separated by about 4 cms from the housing so that the housing is easily held by one hand. Switch $S_4$ is arranged at the upper end of the handle so that it is easily operated by the thumb. Switches $S_1$ and $S_2$ and meter M1 are positioned above the handle and the battery, capacitor, oscillator and other circuit components are arranged within the housing.

Electrode $P_2$ is formed by the body of the main housing and so may be held against the patient with the handle in the upright position. A clip 53 is provided at the base of the main housing so that, when the apparatus is not in use, the second housing 54 containing electrode $P_1$ may be clipped to the main housing and the apparatus transported as a single unit.

Figure 3:
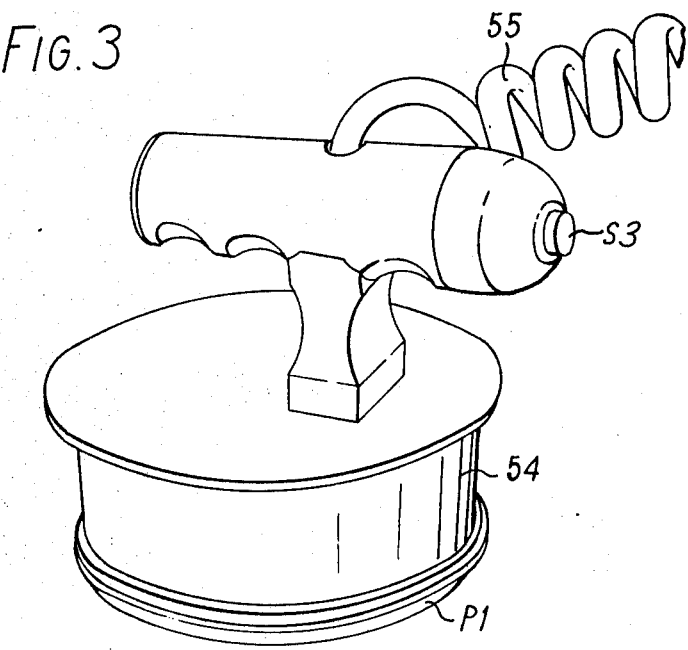
FIG. 3 is a view of the other housing of the defibrillator of FIG. 1.
Figure 4:
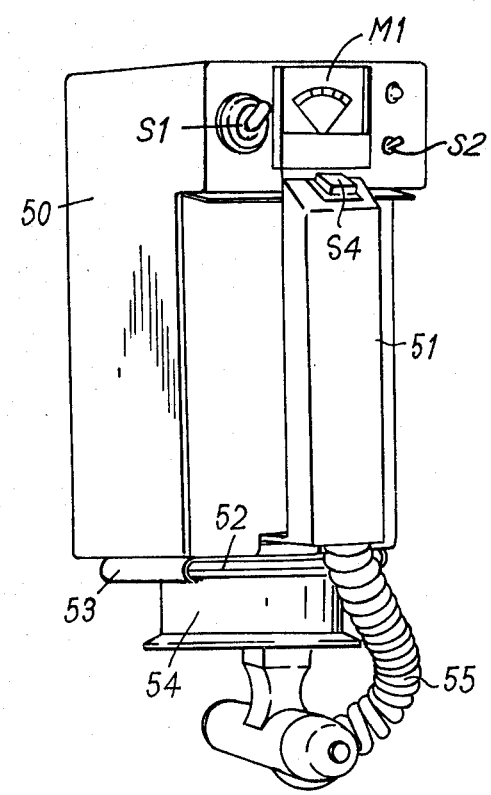
FIG. 4 is a view of the defibrillator with the housings clipped together.

The second housing 54, shown in FIG. 3, comprises the electrode $P_1$, switch $S_3$ and the choke L1, the latter being situated within the housing, and is connected to the main housing by leads 55. When the second housing is removed from clip 53 both electrodes may be pressed against the patient's body, the capacitor having been charged previously to the required potential, and the capacitor discharged through the patient by simultaneous operation of switches $S_3$ and $S_4$. As may be seen from FIG. 3, switch $S_4$ is readily operable by the thumb while the second housing is pressed against the patient.

The potential, capacitor and inductance are preferably such that the voltage wave-form across the electrodes of the discharge pulse has a duration from 10 to 16 milli-seconds, a peak value of not more than 4 kilovolts and a minimum rise time to that peak of one thousand micro-seconds when the electrodes are connected across a load resistance of between 50 and 75 ohms representative of a patient. Said rise time is preferably not less than 1100 micro-second. Such values may be achieved by the use of a capacitor having a value of 50 micro-farads, and an inductance having an inductance value of 50 milli-henries and an ohmic resistance of 18 ohms.

It will be understood that relays RL1 and RL2 are required to withstand high voltages in operation and they are preferably of the sealed gas-filled type.

We claim:

1. A defibrillator apparatus comprising a capacitor, charging means including a direct current source arranged to charge the capacitor to a given energy level, an inductance and a pair of electrodes arranged to be connected by switch means to said capacitor, one by way of said inductance, whereby the capacitor may be discharged through a patient by means of the electrodes to inflict an electric shock on that patient, the selection of the energy level, the capacitor and the inductance being such that the voltage wave-form across the electrodes of the discharge pulse has a predetermined duration, peak value and rise time when the electrodes are connected across a load resistance which corresponds to that of a typical patient, each of said electrodes being mounted as at least a portion of a respective housing which may be placed in contact with the patient, and the charging means, inductance, capacitor and any other circuit components used in the defibrillator being contained in or on said housings so that the apparatus is fully portable.

2. Apparatus according to claim 1, in which the energy level, capacitor and inductance are selected such that the voltage wave-form across the electrodes of the discharge pulse has a duration from 10 to 16 milliseconds, a peak value of not more than 4 kilovolts and a minimum rise time to that peak of one thousand microseconds when the electrodes are connected across a load resistance of between 50 and 75 ohms representative of a patient.

3. Apparatus according to claim 1, in which the inductance is mounted within one of the housings and substantially all of the other circuit components are mounted in the other housing.

4. Apparatus according to claim 1, provided with means for removably attaching the housing together so that the apparatus may be carried with one hand.

5. Apparatus according to claim 1, in which said means for charging the capacitor comprises a storage battery, an oscillator arranged to be driven from the battery to produce an AC voltage output, a rectifier and voltage multiplier circuit connected to the oscillator to produce the required voltage for charging the capacitor to said potential and a relay arranged to connect one plate of the capacitor either to said voltage multiplier circuit or to one of said electrodes.

6. Apparatus according to claim 5, in which said relay is operable by means of a pair of switches arranged in series and disposed one on each housing.

* * * * *